(12) United States Patent
Sun

(10) Patent No.: US 7,645,462 B2
(45) Date of Patent: Jan. 12, 2010

(54) ACUPOINT PATCH

(75) Inventor: Liqin Sun, San Gabriel, CA (US)

(73) Assignee: 3T Herbtech, Inc., San Gabriel, CA (US)

( * ) Notice: Subject to any disclaimer, the term of this patent is extended or adjusted under 35 U.S.C. 154(b) by 1185 days.

(21) Appl. No.: 10/648,026

(22) Filed: Aug. 26, 2003

(65) Prior Publication Data

US 2004/0043062 A1 Mar. 4, 2004

Related U.S. Application Data

(60) Provisional application No. 60/406,557, filed on Aug. 27, 2002.

(51) Int. Cl.
*A61K 36/00* (2006.01)
*A61L 15/16* (2006.01)
*A61F 13/02* (2006.01)
*A61F 13/00* (2006.01)
*A61K 9/70* (2006.01)

(52) U.S. Cl. ............... 424/725; 424/447; 424/448; 424/449; 424/779

(58) Field of Classification Search ............ 128/156, 128/155; 604/306
See application file for complete search history.

(56) References Cited

U.S. PATENT DOCUMENTS 4,592,753 A * 6/1986 Panoz .................. 424/449
4,858,604 A * 8/1989 Konishi ................. 602/57
2003/0082214 A1 * 5/2003 Williams et al. ......... 424/400

FOREIGN PATENT DOCUMENTS

| CN | 1113149 A | * 12/1995 |
| JP | 11158081 A | * 6/1999 |
| JP | 2000044481 A | * 2/2000 |
| WO | WO 9926571 A1 | * 6/1999 |
| WO | WO 0187276 A1 | * 11/2001 |

OTHER PUBLICATIONS http://www.3t-herb.com/html/oculax.html. OCULAX™ Acupoint PAtch for Eye Relaxing. Copyright 3T Herbtech Inc. 2000. pp. 1-5.*

* cited by examiner

*Primary Examiner*—Christopher R Tate
*Assistant Examiner*—Amy L Clark
(74) *Attorney, Agent, or Firm*—Michael Fedrick; Sheldon Mak Rose & Anderson

(57) ABSTRACT

A method, apparatus and method of making acupoint patches is disclosed. The acupoint patch of the present invention uses natural herbs as raw materials. It is made by combining traditional Chinese acupuncture therapy and contemporary transdermal controlled release technologies. The acupoint patch of the present invention is made with natural herb extracts using contemporary transdermal absorption technologies based on the characteristics of different acupoints. They can stay on the skin for 6-8 hours, during which period natural herb essence enters blood circulation and performs a sustainable regulating function. This is a feature unrivaled by traditional acupuncture.

9 Claims, 4 Drawing Sheets

Blood medicine concentration (in ng/ml) vs. Application time (h)

Blood medicine concentrations of two patients applied with 2% monarkite plasters (application area 10 $cm^2$)

Blood medicine concentration peak/trough phenomenon.

Blood medicine concentration (Y-axis) vs. Time

A. Medicine effective duration
B. Excessive medicine concentration duration

Regular medicine application method is used

Steady blood medicine concentration of TTS

A. Oral medicines   B. Acupuncture   C. Oculax

Flowchart of Herb Extraction Process

ACUPOINT PATCH

RELATED APPLICATION

The present invention claims priority from provisional application, Ser. No. 60/406,557, filed on Aug. 27, 2002, entitled ACUPOINT PATCH. The entire disclosure in this provisional application is incorporated herein by reference as if fully set forth herein.

RELATED FIELD

The present invention relates to herbal medicine and more particularly relates to therapeutic patches which are applied various locations of patients for therapeutic purposes.

ART BACKGROUND

For a long time, herbal medicine and herbal treatment in China have enjoyed seemingly mythical healing powers. As early as over three thousand years ago, BIAN Que and HUA Tuo, both prestigious doctors of Chinese medicine, have applied the fundamental principles of "stimulating blood circulation for relaxing muscles and joints" to stimulating acupoints on a patient's body for relaxing and easing purposes.

As will be described in the present application, the essences of natural herbs are extracted to make therapeutic patches of the present invention, based on the principles of Chinese medicine and acupuncture. When applied to acupoints around the eyes, the patches of the present invention can achieve an effect similar to, and yet better than, that of acupuncture. The patches of the present invention can relax muscles, nerves and blood vessels around the eyes through painless and easy application. The also help alleviate eye fatigue and give the patient a better vision.

Acupoints

Acupuncture, with a history dating all the way back to several thousand years in China, is now widely recognized in western medical filed. During recent years, scientists have done researches as well as anatomic, histochemical, and algesia physiologic experiments based on contemporary medical knowledge while continuing the development of acupuncture. Phenomena and the nature of the main and collateral channels have been studied from different perspectives. Issues such as the connection between acupuncture points and feelings, as well as that of acupuncture points and body organs have been researched to promote the benefits of combining acupuncture and contemporary medical science. As such, acupuncture has been a focus of international medical field. It is known to all that acupuncture cures diseases by stimulating specific locations, namely acupoints, of the body. Why is acupuncture applied to acupoints, instead of other parts of the body? A brief introduction is as follows.

The nature of acupoint energy substance is a cytology and biochemistry issue. Recent researches indicate that main and collateral acupoints are points consisting of cells containing a relatively large amount of adenosine triphosphate (ATP). Adenosine is the factory that generates power for the cells. It contains abundant ATP synthetic enzyme and is capable of producing a large amount of ATP energy. During experiments, tissue cells taken from such acupoints such as Zusanli, Hegu and Quchi, as well as from non-acupoint locations were dyed and observed under microscope. Comparison indicated that the adenosine inside these cells increased and showed no deformity. Therefore, we can draw the conclusion that an increasing amount of good quality adenosine can produce a large amount of ATP energy and enhance the functions of different organs and fluid mobility. When acupoints are stimulated with needles, or other objects such as medicated patches, this system will produce a large amount of good quality energy to provide for and to carry different necessary substances and nutrients.

The Nobel Prize in Chemistry was awarded, in 1997, to two scholars for their elucidation of the enzymatic mechanism underlying the synthesis of adenosine triphosphate (ATP). One of the researchers who studied cell passage ions had verified the mechanism of acupuncture. In addition to a large amount of good quality adenosines, low cell electrical resistance and high current magnitude, channel and acupoint cells are also featured with good membrane permeability, more intercellular passages, good cell viability and complete ATP synthetic enzyme.

Recent studies of channel and acupoint functions have provided additional inspirations. Researches have indicated that the concentrations of calcium ions (Ca++) at channels and acupoints are higher than non-channel or acupoint locations. It has been found through experiments that stimulating a certain channel with needles resulted in increase of calcium ion concentrations at other acupoints on this channel. When any pathological change exists in a certain organ, the calcium concentrations at surrounding acupoints experienced abnormal changes, which proved that calcium ion was a key indicator of channel movements. In addition, Xiao-Song G U, et al., have recently found that electronic microscope observation of the differential protein of sensory nerve indicated that 29 KD protein was only found in the cyton and process of level I sensory neurons. Stimulating acupoints resulted in the secretion of active substances and enhanced the bridging function of 29 KD protein. The amount of information passing through the channels increased, resulting in strong interactive stress and achieving internal balance. 29 KD protein transmits more than just biological electrical signals. It can also transmit a variety of ion substances or small molecule substance. This kind of transmission is completed through continuous transmission by 29 KD protein. This is the mechanism underlying the effect of stimulating channels and acupoints.

Disadvantages of Acupuncture

Acupuncture has a history of over three thousand years in China. Over three thousand years ago, Chinese doctors started to cure different diseases with acupuncture. Recently, acupuncture has been widely used to treat eye diseases and ailments. The mechanism of alleviating and curing eye diseases involves regulating the channels and the vegetative nervous system. Then observation is on the artery peripheral plexus and the capillary artery front plexus formed by adrenalinergic nerves and cholinergic nerves around the small blood vessels distributed at certain acupoints with fluorescence organ chemical method. Experimental morphology proved that they were all fibers of sympathetic ganglions with the functions of controlling peripheral circulation resistance and local blood circulation. Using histological method, it was also observed that the cholesterase small nerve tracts consisting of the primitive marrow fiber inside the axiom nerve branches penetrated to deep underneath the acupoints, and extended to close to the capillary artery along to the small artery and vein before forming free ends. They then joined the capillary wall nerves and the vegetative nerves. Therefore, sympathetic nerves are considered an important part of the channels.

Acupuncture cures eye diseases by stimulating acupoints around the eyes and adjusting functions of the vegetative nerves. Microcirculation is promoted, and so is oxygen and nutrients transmission around the eye acupoints. Microcirculation stasis is alleviated, and the ancillary muscles around the eyes are regulated and relaxed. This results in complete regulation and adjustment of the eyes. In the meantime, it also helps reduce tension of cerebral cortex and thus achieves relaxation, as well improves sleep and memory.

Acupuncture has represented an essential part of traditional Chinese medicine. Its healing powers and effects have been widely recognized. We all know that in acupuncture, needles are used to stimulate acupoints for promoting blood circulation and relaxing nerves and muscles. Therefore, many ailments, discomforts or sicknesses can be cured with acupuncture therapy. Many people have become aware that acupuncture has an advantage in relieving pains and regulating immunity that is not matched by western medicines. However, acupuncture has its disadvantages too. First, although they are aware of the benefits of acupuncture, many people refuse to accept it as a therapy because of their phobia of pain, namely from the needles. Unable to overcome the fear of needles, they have no choice but to avoid acupuncture altogether. To these people, acupuncture is good, but it would only be perfect if it would not cause any pain. Second, recent reports have pointed out that acupuncture is only capable of relaxing local areas and the effects are temporary too. Why? In acupuncture, the needles stay for 20-30 minutes. In about two hours after treatment is finished, the effect of acupuncture starts to diminish. One cannot work or sleep while carrying needles on the body. How to extend the effect of acupuncture has become a new research subject. As will be described in the following, the present invention by inventor Liqin SUN can replace needles. While reducing the pain resulted from treatment, it also expands the scope of treatment. It is essentially "acupuncture without needles."

SUMMARY OF THE PRESENT INVENTION

A method, apparatus and method of making acupoint patches is disclosed. The acupoint patch of the present invention uses natural herbs as raw materials. It is made by combining traditional Chinese acupuncture therapy and contemporary transdermal controlled release technologies. It originates from acupuncture but easily surpasses acupuncture. As the essence of traditional Chinese medicine, acupuncture has been studied and developed during recent years to achieve better effects and minimum side effects. Acupoint patch application in accordance with the present invention now reaches beyond what acupuncture therapy can deliver.

As will be described herein, the acupoint patch of the present invention is made with natural herb extracts using contemporary transdermal absorption technologies based on the characteristics of different acupoints. They can stay on the skin for 6-8 hours, during which period natural herb essence enters blood circulation and performs a sustainable regulating function. This is a feature unrivaled by traditional acupuncture. As previously mentioned, acupuncture can only relax ciliary muscles (effective on pseudomyopia) and only has a temporary effect. The reason is because in acupuncture, the needles only stay for 20-30 minutes. In about two hours after the treatment finishes, the effect of acupuncture starts to diminish. The successful experiment of the acupoint patch of the present invention has overcome the problem of the temporary effect of acupuncture therapy. It is also the first painless therapy. Patients only need to apply the acupoint patch of the present invention to designated acupoints on the face (Zanzhu, temple, Sibai) before bedtime to achieve the desired results.

Also, application of the acupoint patch of the present invention is easy and safe. It is suitable for patients of different ages. In addition, the acupoint patch of the present invention not only has the transdermal absorption feature of traditional plasters, but also uses controlled release technologies so that the herbal nutrients enter blood circulation at an even speed, to ensure consistent blood medicine concentration and to avoid blood medicine concentration peak/trough problem.

DETAILED DESCRIPTION OF THE PREFERRED EMBODIMENTS

A method, apparatus and method of making medicated patches is disclosed. In the description that follows, numerous terminology in herbal medicine, acupuncture and acupoints will be referenced, using terms familiar to those skilled in the art. Also, the phrase "acupoint patch" and Applicant's trademark "Oculax™" are used interchangeably in the present application, as they both refer to the transdermal acupoint patches for the controlled release of herbal extracts through the acupoints of a patient's body.

Disadvantages of Traditional Plasters

Transdermal medicine has been used in therapies as early as in the ancient times. Traditional Chinese plasters are some of the examples. Plasters help overcome the problems of pain and time limitation of acupuncture. However, the effect of plasters is less desirable than that of acupuncture, due to their limited permeability. In addition, although traditional plasters do have some of the characteristics of transdermal patches, the dosages are usually not precise. Precise control and maintenance of the desired blood medicine concentration are difficult to achieve, thus resulting in unbalanced blood medicine concentration (concentration peaks and lows). That is to say, during the first two hours after plasters are applied, the amount of medicine entering blood circulation is higher than the required amount, whereas after two hours, the amount of medicine entering blood circulation becomes insufficient.

Figure 1:
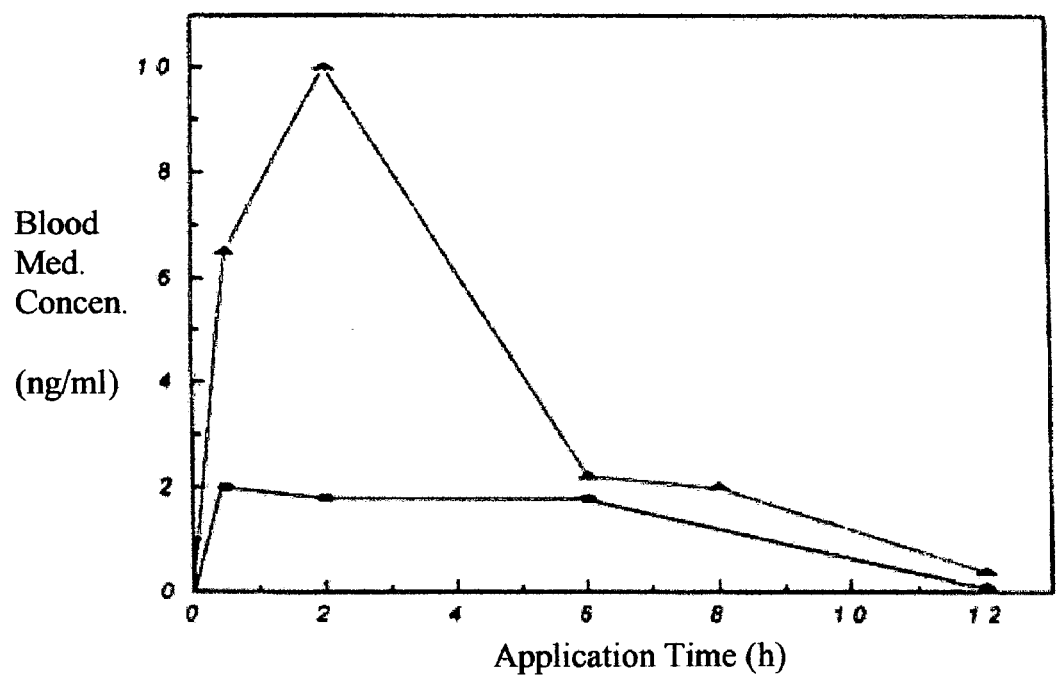
FIG. 1 illustrates the blood medicine concentration (in ng/ml) vs. application time (in hour).

In our experiment, we applied 2% monarkite plasters of the same size to two patients. Their blood medicine concentrations differed by several times. This was due to inaccurate plaster thickness as well as different physiques of the patients. FIG. 1 illustrates the blood medicine concentration (in ng/ml) vs. application time (in hour).

OCULAX™—Acupoint Patch of the Present Invention

The acupoint patch of the present invention, commercially called OCULAX™, uses natural herbs as raw materials. It is made by combining traditional Chinese acupuncture therapy and contemporary transdermal controlled release technologies. It originates from acupuncture but easily surpasses acupuncture. As the essence of traditional Chinese medicine, acupuncture has been studied and developed during recent years to achieve better effects and minimum side effects. Acupoint patch application in accordance with the present invention now reaches beyond what acupuncture therapy can deliver.

As will be described herein, the acupoint patch of the present invention is made with natural herb extracts using contemporary transdermal absorption technologies based on the characteristics of different acupoints. They can stay on the skin for 6-8 hours, during which period natural herb essence enters blood circulation and performs a sustainable regulating function. This is a feature unrivaled by traditional acupuncture. As previously mentioned, acupuncture can only relax ciliary muscles (effective on pseudomyopia) and only has a temporary effect. The reason is because in acupuncture, the needles only stay for 20-30 minutes. In about two hours after the treatment finishes, the effect of acupuncture starts to diminish. The successful experiment of the acupoint patch of the present invention has overcome the problem of the temporary effect of acupuncture therapy. It is also the first painless therapy. Patients only need to apply the acupoint patch of the present invention to designated acupoints on the face (Zanzhu, temple, Sibai) before bedtime to achieve the desired results.

Also, application of the acupoint patch of the present invention is easy and safe. It is suitable for patients of different ages. In addition, the acupoint patch of the present invention not only has the transdermal absorption feature of traditional plasters, but also uses controlled release technologies so that the herbal nutrients enter blood circulation at an even speed, to ensure consistent blood medicine concentration and to avoid blood medicine concentration peak/trough problem.

Acupoint Patches (OCULAX™) in More Detail

There have been plenty of conventional healthcare products directed at preserving vision, relaxing eyes, improving sleeping patterns, and alleviating eye fatigue. Most of these conventional products are taken orally. The acupoint patch of the present invention is made of pure natural herb extracts by combining traditional Chinese acupuncture and contemporary transdermal absorption controlled-release technologies. The acupoint patch in accordance with the present invention is a product with the following important implementation features:

1. Use of advance technology:
  A. It combines acupoint therapy principles in traditional Chinese acupuncture;
  B. It uses the state-of-the-art transdermal absorption controlled release technologies available only from the recent years;
  C. It is made of natural herb extracted with nano-technology;
  D. It is a multi-layer, e.g. five-layer patch.
2. Characteristics in application of acupoints:
  A. Patch application acupoints include Zanzhu, temple, Sibai, Fengchi, Jingming, Touwei, Yinxiang, Yingtang, Yifeng and Anmian;
  B. The acupoint patch is applied to the designated acupoints before bed time and taken off on the following morning. The application time is 6-8 hours.
  C. The acupoint patch can be applied at any time without causing any pain.
3. Characteristics in raw materials used:
  Raw materials include pure natural herbs such as Tangkuei (*Angelica sinensis*), Ligusticum (*Ligusticum wallichii*), chrysanthemum, and *Salvia* root (*Salvia miltiorrhiza*). These ingredients have no side effect of whatsoever. Tangkuei, *Ligusticum*, chrysanthemum and *Salvia* root can all promote blood circulation, regulate nervous system and reduce muscle spasm.
4. General characteristics:
  A. Acupoint patch helps achieve all the benefits of painless acupoint therapy.
  B. Transdermal absorption controlled-release technology are used to avoid the blood medicine concentration peak/trough effect of traditional oral medicines.

The unique characteristics of the acupoint patch of the present invention are attributable to the fact that it is the combination of traditional Chinese acupuncture and modern technologies. It follows both the principles of traditional Chinese acupuncture—applying natural herbs at acupoints—and combines modern transdermal absorption controlled-release technologies. As a result, Oculax can release effective ingredients at the acupoints consistently for a relatively longer period of time, and thus, regulate the nerves, muscles, and blood vessels around the eyes and in the head to promote eye and head blood circulation and to achieve the goal of relaxation. It helps in different types of eye problems, such as dry eyes, eye fatigue, vision deterioration, photoesthesia and tearing, myopia, presbyopia, glaucoma, and cataract. It also alleviates migraine, dizziness and insomnia. It is the textbook example of combining Chinese medicine with western medicine. Oculax has surpasses the conventional oral medicines or eye drops and opened up a new era for eye maintenance products.

The acupoint patch of the present invention may be made of natural herbs such as *Ligusticum*, Tangkuei, *Salvia* root, and chrysanthemum. Records in pharmacopoeia, e.g. ZUENG Hu-Zhan et. al, MODERN STUDY OF TRADITIONAL CHINESE MEDICINE, Vol. 1-6, Xue Yuan Press, Beijing, China, 1999, ISBN 7-5077-1320-2, indicate that they have the following functions:

*Ligusticum*—Promote blood and Qi circulation. *Ligusticum* can remarkably increase brain blood flow and improve mater microcirculation and flow. It has an evident effect in alleviating chronic microcirculation disturbance, especially bulbar conjunctiva microcirculation disturbance.

Scholars have observed the effect of *Ligusticum* drops on the brain blood circulation speed of cerebral arteriosclerosis patients using cranial Doppler ultrasound instrument. Twenty-one cerebral arteriosclerosis patients were given *Ligusticum* drops. The changes of their brain blood vessels and brain blood circulation speeds were observed using cranial Doppler ultrasound blood flow analyzer. The results indicated that *Ligusticum* drops could remarkably improve the vasomotion functions, lower blood viscosity, and promote brain blood circulation of cerebral arteriosclerosis patients. This indicates that *Ligusticum* is a good product for prevention of cerebral arteriosclerosis.

Researches have also been done using *Ligusticum* injection to treat bulbar conjunctiva microcirculation disturbance due to cerebral thrombus. Ten thrombus patients were given intravenous injection of 10 ml of 10% *Ligusticum*. Before injection, bulbar conjunctiva microcirculation was observed using regular method. The results indicated that alleviation of bulbar conjunctiva microcirculation disturbance was evident after *Ligusticum* was injected, mainly reflected in improved flow, faster circulation, reduced cell concentration or free accumulation. These results were seen 20 minutes after *Ligusticum* was injected and was the most evident in 60 minutes after the injection. In addition, *Ligusticum* also has a remarkable effect of dilating blood vessels.

*Salvia* Root—Promote blood and Qi circulation, remove blood stasis and alleviate pain, promote micro blood circulation. It has a remarkable effect in improving microcirculation, especially eye bulbar conjunctiva microcirculation.

Experiments have proven the effect of *Salvia* root extract on treating microcirculation disturbance. Salvia root extract can remarkably dilate the capillaries of rabbits with microcirculation disturbance. In the experiment, rabbits that had been given intravenous injections of 10% macromolecule dextrose were given *Salvia* root extract. The effect of *Salvia* root extract on the capillaries and plasma lactic acid content was observed. The results indicated that intravenous injection of different dosages of *Salvia* root and *Salvia* root essence could both promote the blood circulation of rabbits with eye bulbar conjunctiva microcirculation disturbance and mesenterium microcirculation disturbance. It also helped in peripheral circulation and thus, alleviated metabolism problem caused by cell ischemic problem and anoxia.

Researches have also indicated that *Salvia* root has an anti-aging function. Scholars have compared the effects of *Salvia* root and vitamin E on the SOD and LPO of aged rats. The effects of *Salvia* root are better than those of vitamin E. The results indicated that *Salvia* root could evidently improve the activity of the erythrocuprein in the red cells, heart, liver and kidney of aged rats (P<0.01). Salvia root also remarkably lowered the content of peroxide fat in the serum, heart, liver and kidney of the same aged rats (P<0.01). Compared with vitamin E, Salvia root has better effects.

Tangkuei—Promote blood and Qi circulation. Major results include improved flow, faster flow speed and improvement of fundus blood circulation. Experiments and researches indicated that Tangkuei is the ideal ingredient to regulate blood vessel functions. Tangkuei can dilate peripheral blood vessels, lower blood resistance, and improve blood circulation. Experiments have shown that Buerger's disease patients experienced improvement of blood circulation after one month of Tangkuei injection. The effective rate is 60%.

Researches have proven that the effective ingredient of Tangkuei is ferulic acid, which can dilate separated major arteries. Sedated animals were given intravenous injection of 50 mg/kg ferulic acid sodium. Arteria femoralis blood circulation was increased and external blood vessel resistance was reduced. Japanese scholars have proven through experiments that in addition to regulating blood pressure, Tangkuei can also lower eye pressure and reduce ventricular water production. Therefore, this effect is considered attributable to both peripheral and central factors.

Other researches indicate that brewed Tangkuei soup can remarkably improve learning memory of white rats. The memory of rats was observed using passive avoidance conditioned reflex—diving platform experiment. The results indicated that memories of rats and repeated response abilities of rats were improved to different degrees.

Chrysanthemum—Improve vision and refresh, eliminate wind and clear heat. It can be used to treat red eyes, swelling and pain, headache and insomnia, and blurred vision and dizziness. It can dilate blood vessels, increase blood flow and delay the aging process.

Experiments have proven that chrysanthemum injection can dilate blood vessels and increase blood flow. Thoracic sedated cats were given intravenous injection of 1.5-2.0 g/kg of chrysanthemum. Coronary venous sinus flow was increased by 93% immediately. During the 40 minutes of continuous observation, the coronary flow was increased as compared to that before the injection. In separated rabbit heart perfusion application, the coronary flow was increased by 61% and 53% respectively in one minute and three minutes after application of medicine as compared to that before the application. Chrysanthemum injection can also remarkably dilate skin and organ blood vessels. Based on this, chrysanthemum is used in Oculax to improve blood circulation and to increase oxygen and nutrients supply to the eyes and the brain blood vessels.

Researches have proven the anti-aging function of chrysanthemum. Experiments were done to observe the effect of chrysanthemum immersion liquid on young silkworms. Results indicated that in addition to extend the age, chrysanthemum immersion liquid could also increase length and weight of silkworms and promote their development. This proves that chrysanthemum has an anti-aging function.

The above natural herbs have no side effect. When applied at night for 6-8 hours, the natural nutrients can enter blood circulation through the skin to relax nerves, blood vessels and muscles around the eyes and to alleviate eye fatigue. They can promote brain blood circulation, help in sleep and improve memory.

While these natural herbs currently come from China and/or the United States, other sources may be available to those skilled in the art of extracting herbal essences based on the description herein. All these materials are pure natural herb extracts, and their specific information are provided in Tables 1-4 of the present application.

Transdermal Controlled-Release Patch

Technical characteristics of the acupoint patches are as follows: Due to excessive toxins or ineffective peak/trough medicine concentration of regulation medication methods (oral taking, injection, etc.), controlled release technologies have attracted more and more attention. During the past ten years, researches on controlled medicine release have developed rapidly. A significant aspect of such researches—transdermal treatment system, has experienced the most radical development and become a new star using the highest technologies. The acupoint patch of the present invention is a patch made of natural herbs using transdermal absorption method. It is directly applied to acupoints around the eyes and features characteristics not possessed by oral medicines or eye drops. Preferably, the acupoint patch of the present invention has five layers with different natures and functions, as will be described below:

1. LINING LAYER: Impermeable to medicines, provide protection and supporting functions.

2. STORAGE LAYER: Medicines are evenly distributed at this plastics layer.

3. CONTROLLED RELEASE LAYER: Serves to control and release medicines at the required speed.

4. PRESSURE SENSITIVE LAYER: Attaching the acupoint patch to the skin can provide an explosive dosage of medicine so that medicines can saturate the cuticle quickly and enter into body blood circulation.

5. PROTECTION AND NON-STICKING LAYER: Remove this layer, before applying the acupoint patch to the patient's acupoint(s).

Quality Standards

The following quality specifications may be adopted for ensuring the quality of acupoint patches of the present invention:

1. APPEARANCE: The acupoint patch is a round patch with one side coated with self-adhesive medicine film. Each patch is 2.27 square centimeters.

2. DIMENSION: Each set consists of six round patches attached to 4×7 centimeter non-sticking plastics protection film. Each patch is dark brown patch. Even medicine layer of consistent color should be observed in any indoor location without direct sunlight. There should be no detachment of the medicine layer. The plastics side should be even, clean and free from areas not covered by medicines.

3. INGREDIENTS: The main ingredients of each set of patches include *Ligusticum, Salvia* root, Tangkuei and chrysanthemum. Other materials used include polyacrylic acid medical pressure-sensitive glue and polyester lining film.

4. FUNCTIONALITY: Relax nerves and muscles, refresh, alleviate fatigue, promote blood and Qi circulation, and distribute and minimize bodily heat.

5. SPECIFICATION:

a. Weight variance: Take three sets of patches (total 18 pieces). Remove patches from the adhesive layer. Weigh each piece with 1/10000 balance and calculate the average weight. Compare the weight of each piece. The number of patches with a weight variance over +5% shall not exceed two. No weight variance exceeding +10% is allowed.

b. Area of the patch: Take five patches. Measure the diameter of each round patch and calculate the area. The area of each set may not be less than 2.2 square centimeters (the sum of six patches.)

c. Heat resistance and stability test: Place five patches in a freezer at −5° and take out in 20 minutes. Touch with hand. The patches should feel sticky.

d. Cold resistance and stability test: Place five patches in a freezer at −5° and take out in 24 hours. Warm up to room temperature and touch with hand. The acupoint patches should feel sticky.

Additional Advantages of Acupoint Patch of the Present Invention

The acupoint patches of the present invention can achieve consistent application of medicines. Medicines released at a controlled speed enter body circulation consistently and steadily. This helps avoid peak/trough blood medicine concentrations of other medicine application methods and gives full play to the curative and regulating functions of the medicines. Since the medicines do not pass the digestive tract, destruction of the natural herb ingredients by pH, food and digestive fluids is avoided. Intestine or stomach upset, poor absorption and side effects of the metabolites due to stimulation of the digestive tract are also avoided. In addition to controlling medicine release, patients may also apply Oculax based on their conditions.

Figure 2:
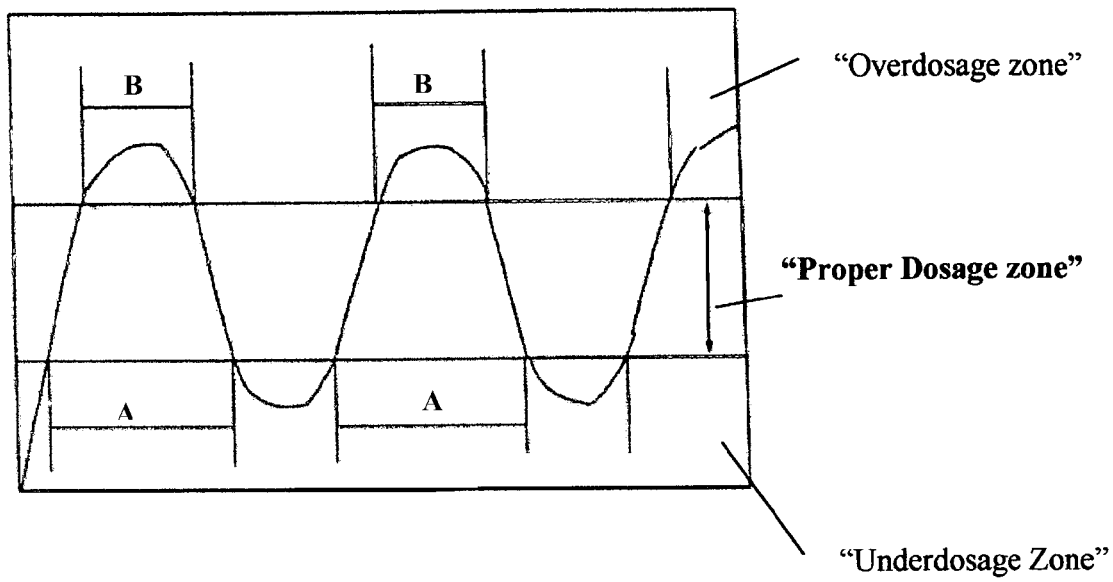
FIG. 2 illustrates blood medicine concentration with peak and trough phenomenon.
Figure 3:
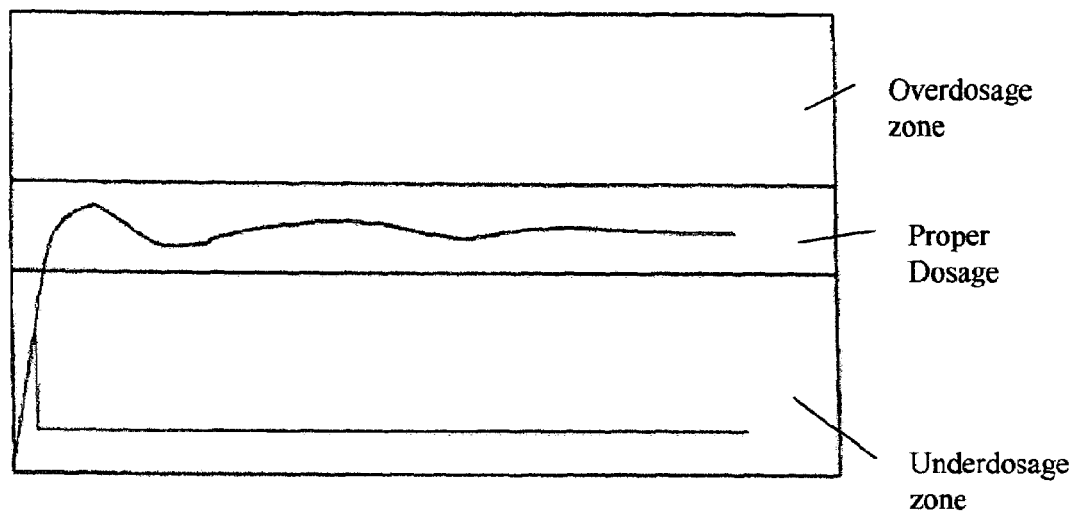
FIG. 3 shows steady blood medicine concentration over time, where the treatment zone is more stabilized.

FIG. 2 shows blood medicine concentration with peak and trough phenomenon. FIG. 3 shows steady blood medicine concentration over time, where the treatment zone is more stabilized.

The acupoint patch of the present invention brings out the curing effects of short biological half-life medicines that cannot be easily applied through oral taking or injection, as well as medicines with narrow "treatment window", while limiting their side effects.

Since the medicines do not pass the digestive tract, destruction of the natural herb ingredients by pH, food and digestive fluids is avoided. Intestine or stomach upset, poor absorption and side effects of the metabolites due to stimulation of the digestive tract are also avoided.

The preliminary filtering function of the liver is bypassed to avoid dissolution of medicines by the liver and damage to the liver caused by medicines.

The acupoint patch of the present invention is easy to use. It can be applied or removed based on the patient's need. It is painless and easily accepted by the patients.

The acupoint patch can regulate eye nerves, blood vessels and muscles to restore normal eye operation.

As can be appreciated, transdermal controlled medicine release helps achieve predetermined and longer medicine effective time, and improves medicine's effectiveness. Although the dosage is relatively small, Oculax achieves satisfactory results without causing any side effect through transdermal absorption at acupoints. The frequency of medication and total dosage are reduced whereas the effectiveness is improved. This is the optimal eye care product.

Application of the Acupoint Patch

For treatment and care of the eyes, the patches of the present invention should be applied to three sets of acupoints around the eyes every night. The blood vessels, nerves and muscles passing these three sets of acupoints are introduced as follows:

ZANZHU: This acupoint is located at the side above the eyebrows at the corner of the eye sockets. Distributed at this acupoint are frontal artery, vein and the medial lateral branches of facies frontalis.

TEMPLE: This acupoint is located 0.5 centimeter from the tip of the brow. Distribbuted at this acupoint are the temporal branches of nervus facialis, and orbita arteries and veins.

SIBAI: This acupoint is below the pupil at the inferior orbital socket. Distributed at this acupoint are branches of facial arteries and veins. Orbita arteries and veins are distributed around nervus facialis and inferior orbital nerves.

The acupoint patch of the present invention thus helps in absorption of natural herbal nutrients by using acupoint patch mechanism. The acupoint patch of the present invention works via the nerve-incretion-immunity system as follows:

Patch acupoints→Body→Participation by the nervous system, the immune system and the immune system→(feedback)→the body forms a new stable internal environment.

The acupoint patch of the present invention uses natural herb extracts as raw materials. It is made based on the mechanism of acupuncture and contemporary transdermal controlled medicine release technologies. With the advantages of the acupoints and the transdermal controlled medicine release, Oculax can release medicines into blood vessels, nerves and muscles around the eyes in a short time without the pain of acupuncture. It saves time and improves vision-regulating effectiveness. Oculax is truly an acupuncture therapy without needles.

Oculax application instructions: Apply Oculax to the six designated acupoints (two on Zanzhu, two on the temples and two on Sibai) every night before sleep. Oculax stays for 6-8 hours. During these 6-8 hours, the natural herb nutrients enter blood circulation directly through the acupoints at an even speed. The result is much better than that of 30 minutes of traditional acupuncture. It also solves the problem of short needle-staying time.

The scientific features of the acupoint patches of the present invention. Based on conventional concepts, people usually take some nutrients such as vitamin A or comprehensive vitamins to care for their eyes. Orally taken nutrients are dissolved in the livers and the kidneys. Most of the nutrients are discharged and only 10-20% is absorbed. Even less nutrients actually reach the eyes and the effects are seen slowly. Other people use eye drops as eye care. However, eye drops only have a temporary relaxing effect and are therefore, not able to solve the problems. Since eyes are nerve end organs, regulating acupoints around eyes is the optimal method to alleviate eye fatigue. From the anatomy point of view, applying medicines around the eyes brings about the best effects. Oculax patches are applied to acupoints around the eyes. Medicines enter the blood circulation in the fastest manner to achieve the goal of regulating. In addition, it is believed in contemporary medical science that the biological effectiveness of acupoint patches is better than that of oral medicines because of the natural herb nutrients sensitivity and amplification effects of the acupoints. Oculax can promote local and general blood circulation, enhance metabolism, and improve local nutrition, cell immune and fluid immune functions.

Figure 4:
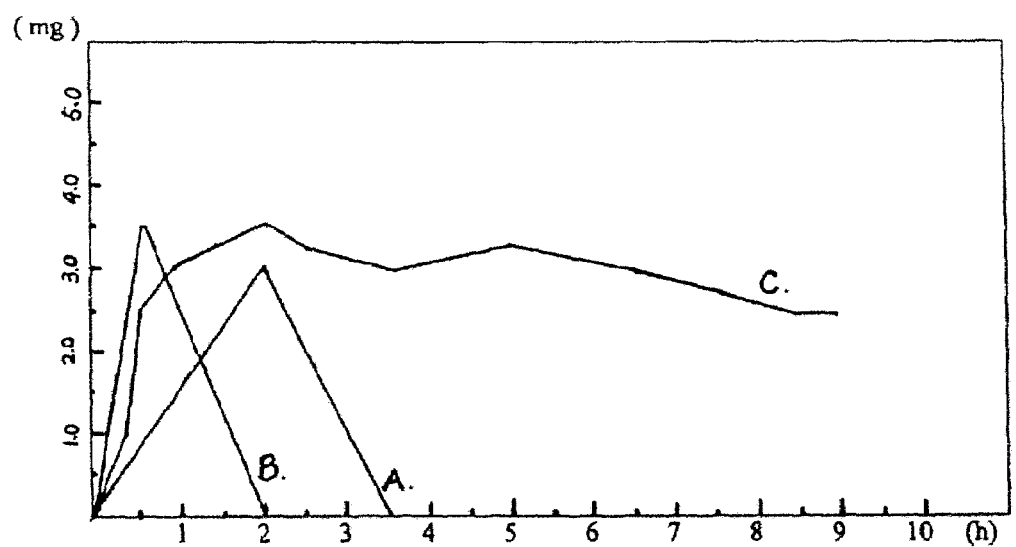
FIG. 4 illustrates a comparison of the acupoint patch of the present invention and other products in terms of blood medicine concentration vs. time.

FIG. 4 illustrates a comparison of Oculax and other products in terms of blood medicine concentration vs. time. Note that Curve A represents oral medication, Curve B represents acupuncture, and Curve C represents Oculax. From the above figure we can tell that compared with oral medicines and acupuncture, Oculax has a longer and more stable regulating function.

The herbal nutrient content of 6 pieces of Oculax is 60 mg, 40% of which enters blood circulation after released through the skin. This means that approximately 24 mgs work on the eyes. The effect can last 6-8 hours. Among the 60 mg nutrients of oral medicines, 25% is absorbed by the body and only 10-20%, e.g. 1.5-3 mg work on the eyes. The effects can last 2-3 hours. The effect of acupuncture is highly desirable in a short period of time. But the effects only last for this short period of time. The effective time is only 15-20% of that of Oculax.

Additional Application of Acupoint Patches

Acupoint patches using transdermal controlled medicine release present a novel method of treating other ailments and illness. In addition to caring for the eyes, such acupoint patches can also be used at other acupoints to treat other illness, provided that they are applied with the proper herbal extracts. A more detailed description is as follows:

Selection of Acupoints:

Acupoints that can regulate and relax eyes: Zanzhu, temple, Sibai, Jingming, Fengchi Acupoints that can regulate sleep patterns: Anmian, Fengchi, Yifeng, temple Acupoints that can regulate the lungs and the tracheas: Feiyu, Tiantu, Dingchuan, Shenyu Acupoints that can regulate liver metabolism: Qimen, Riyue, Zhangme, Zhongwan, Ganyu, Piyu Acupoints that can alleviate nasal allergy: Yingxiang, Feiyu, Yintang, Dazhui, Bitong Acupoints that can regulate blood pressure: Yintang, Renyin, Fengehi, Yifeng, Dazhui Acupoints that can regulate sexual functions: Qihai, Kaiyuan, Zhongji, Qugu, Qichong, Guilai Acupoints that can treat dementia: Touwei, temple, Fengchi, Yifeng, Yintang Acupoints Selection Method and Related Blood Vessel And Nerve Distribution Yinxiang: Located at the muffle at the same level as the medial point of the outer edge of ala nasi. Passing this acupoint include facial artery and vein branches, as well as branches of nervus facialis and orbital nerves. Regulating this acupoint can alleviate nasal congestion, anosmia, nose bleeding, running nose, facial itching and swelling.

Renying: Next to Adam's apple, located at point A of the neck and the frontal lip of sternocleidomastoid. Passing this acupoint include thyroid gland veins and branches of internal and external carotid arteries. Distributed in the superficial layer are neck nervus cutaneus, nervus facialis, and deep sympathetic nerves. Passing the outer side include nervus hypoglossus and nervus vagus. Regulating this acupoint can alleviate sore throat, panting, and dizziness.

Yintang: Located in the middle point between the two brows. Regulating this acupoint can alleviate headache, carebaria, forehead pain and insomnia.

Fengchi: Located at the pit above sternocleidomastoid. Passing this acupoint include branches of occipital arteries and veins and branches of occipital nervelets. Regulating this acupoint can alleviate headache, insomnia, blurred vision and glaucoma.

Yifeng: Behind the earlobe at the pit between the lower jaw and the processus mastoideus. Passing this acupoint include ear arteries and veins, and ear major nerves. At the deeper level is the nervus facialis node processus mastoideus. Regulating this acupoint can alleviate tinnitus, deafness and blurred vision.

Anmian: Located at the middle point between Yifeng and Fengchi. Regulating this acupoint can alleviate insomnia, dizziness, headache and palpitation.

Dazhui: Located below the processus mastoideus of bertebrae cervicales VII, at the same level as the shoulder. Passing this acupoint include branches of carotid arteries, the back branches of cervical nerve VIII, and the median part of the back branches of thoracic nerve I. Regulating this acupoint can alleviate headache, coughing and panting.

Dingchuan: Located next to Dazhui. Passing this acupoints are the same nerves and blood vessels as those passing Dazhui. Regulating this acupoint can cure asthma and alleviate coughing.

Jingming: Located at the pit above eye corner. Passing this acupoint include inner canthus arteries and veins. At the deeper level are main branches of eye arteries and veins. Passing this acupoint also include upper and lower trochlea nerves. At the deeper level are oculomotor nerves and rock nerves. Regulating this acupoint alleviates tearing, nyctalopia, dizziness, myopia and eye pain.

Qimen: Located below the nipple between ribs VI. Passing this acupoint include intercostal arteries and veins (VI), and intercostal nerves (VI). Regulating this acupoint can alleviate liver pain, abdominal distension, sour regurgitation.

Riyue: Located one rib below Qimen and the nipple between ribs VII. Passing this acupoint include intercostal arteries and veins (VII), and intercostal nerves (VII). Regulating this acupoint can cure choleplania, liver diseases, rib pain and vomiting.

Zhangmen: Located at the side of abdomen below the tip of floating rib XI. Passing this acupoint include end of intercostal arteries (X) and below it is intercostals nerves (X). Regulating this acupoint can alleviate liver pain, abdominal distention, vomiting, indigestion and diarrhea.

Zhongwan: Located on the median of the abdomen, four inches above the navel. Passing this acupoint include arteria epigastrica and vena superior, and the front branches of intercostals nerves (VII). Regulating this acupoint can cure choleplania, liver pain, stomachache, abdominal distention, reduce peristaltic sound, and alleviate vomiting and insomnia.

Feiyu: Located below the processus mastoideus of thoracic vertebra m, 1.5 inches next to Shenzhu (GV12). Passing acupoint include the inner back branches of intercostals arteries and veins. At the deeper level are outer branches. Regulating this acupoint can reduce coughing, panting, chest pain, night sweat, and hot flash.

Ganyu: Located below the crest of thoracic vertebra IX, 1.5 inches next to Jinsuo (GV8). Passing this acupoint include the inner back branches of intercostals arteries and veins, the inner back branches of thoracic nerves IX and X. At the deeper level are the outer branches. Regulating this acupoint can cure choleplania, rib pain, dizziness and back pain.

Piyu: Located below the crest of thoracic vertebra XI, 1.5 inches next to Jizhong. Passing this acupoint include the back branches of intercostal arteries and veins, thoracic nerves XI and XII, the inner back branches. At the deeper level are the outer branches. Regulating this acupoint can alleviate stomachache, choleplania, abdominal distention, vomiting and dropsy.

Shenyu: Located below the crest of lumbar vertebra, 1.5 inches next to Mingmen. Passing this acupoint include the back branches of loin arteries and veins (II), and the outer back branches of loin nerves. At the deeper level are the outer branches. Regulating this acupoint can alleviate dizziness, asthma, dropsy and lower back pain.

Tiantu: Located on the medial point above the sternum. Passing this acupoint include the branches of subcutaneous arteria carotis, thyroid arteries. At the deeper level are tracheas. Behind the manubrium are innominate arteries and aorta. Passing acupoint also include the front branches of supraclavian nerves. Regulating this acupoint can reduce asthma, coughing, sore and swelling throat, aphonia and dry throat.

Yongquan: Located on the pelma at the pit when toes are flexed, near the cross point of the front ⅓ and the back ⅔ of the pelma. Passing this acupoint include deeper arcus plantaris and musculus nerves. Regulating this acupoint can alleviate headache, dizziness, sore throat, dry tongue, hypertension and constipation.

Zhongji: Located on the median of the abdomen, four inches below the navel. Passing this acupoint include branches of superficial napes arteries and veins, the branches of arteria epigastrica and vena inferior, and branches of femoris hypogastric nerves. Regulating this acupoint can cure impotence, frequent micturiction, spermatorrhea, female sexual coldness, morbid leucorrhoea, and menstrual disorder.

Kaiyuan: Located on the median of the abdomen, three inches below the navel. Blood vessels passing this acupoint are the same as those passing Zhong Ji. Passing acupoint include the front inner branches of intercostal nerves XII. Regulating this acupoint can cure spermatorrhea, enuresis, impotence, difficult urination, and menorrhalgia.

Qugu: Located at the middle point of the upper edge of symphysis pubis. Passing this acupoint include branches of arteria epigastrica inferior, obturator arteries, and branches of femoris hypogastric nerves. Regulating this acupoint can cure spermatorrhea, impotence, enuresis, menorrhalgia, and menstrual disorder.

Qihai: Located on the median of the abdomen, 1.5 inches below the navel. The blood vessels and nerves passing this acupoint are the same as those passing Shimen. Regulating this acupoint can cure impotence, hernia, spermatorrhea, diarrhea, amenorrhea and menstrual disorder.

Guilai: Located at four inches below the navel and two inches next to Zhongji. Passing this acupoint include arteria epigastrica and vena inferior as well as femoris hypogastric nerves. Regulating this acupoint can alleviate abdominal pain, and cure impotence, hernia and menstrual disorder.

Qichong: Located at five inches below the navel and two inches next to Qugu. Passing this acupoint include superficial branches of napes arteries and veins and at the outer side are arteria epigastrica and vena. Passing this acupoint are also iliac nerves. Regulating this acupoint can cure impotence, vulva swelling, menorrhalgia and menstrual disorder.

Applying the Patches

The manufacture methods of these patches are the same as that of Oculax. They are also made of natural herb extracts by combining acupuncture and transdermal controlled release technologies. Chinese herbs used include tussilago farfara, perillaseed, tendril-leaved fritillary bulb, fruit of Chinese magnoliavine, fructus ligustri lucidi, golden cypress, Centipeda minima, magnolia flower, radix angelicae formosanae, selfheal, radix achyranthis bidentatae and ramulus uncariae rhynchophyllae.

The patches are to designated acupoints based on their different functions, using the same application method.

Application time is 6-8 hours. The patients may choose to apply at day time or night based on different functions.

The application methods are basically the same as the application methods for Oculax. Minor adjustment may be necessary for different diseases and acupoints, as can be appreciated by those skilled in the art.

Using the Acupoint Patch

The following is an exemplary procedure intended to teach a patient about using the acupoint patches. First, the patient is to wash face and apply to Zanzhu, temple and Sibai, before bed time. For dry skin, the patient should apply skincare product before application of acupoint patches. After getting up the following morning, the patient can remove the patches. The patient applies continuously for ten days, stop for 3-5 days and then continue.

Manufacture Process

The acupoint patches are generally prepared as follows:

1. Preparation of Chinese herbs: Extract essence of *Ligusticum, Salvia* root, Tangkuei and chrysanthemum, dry, grind and screen.

2. Preparation of polyvinyl materials: Process medical flesh color PVC with special physical method. Make self-stick materials with PET.

3. Preparation of polyester film: Coat both side of polyester film (0.09~0.15 mm thick) with medical organic silicon anti-sticking materials. The coating should be even and of an appropriate thickness.

4. Preparation of patches: Pour extracts of *Ligusticum, Salvia* root, Tangkuei and chrysanthemum mixed at the prescribed ratio into medical pressure-sensitive polyacrylic acid latex. Mix even and place in a coating machine for coating. Use PVC film as the base material and polyester film as the lining material. Dry in an oven. Cut into patches with a diameter of 17 mm. Inspect and pack to make finished products.

There are two types of controlled release technologies, the application of which depends on the specific use of those skilled in the art.

1. Mix nitrogen ketone with the prepared herbs and pressure-sensitive latex. Place in a coating machine for coating. This is called transdermal absorption controlled release technology.

2. Coat the PVC material with herbs and put a controlled release film in the medicine layer to slow down the release process. It should be noted that different controlled release methods can be achieved based on different applications.

Exemplary Ingredients of Acupoint Patches

1. An exemplary ratio of the main ingredients is: *Ligusticum* 19 mg (23.75%), *Salvia* Root 17 mg (21.25%), Tangkuei 11 mg (13.75%), Chrysanthemum 33 mg (41.25%).

2. Other herbs can be added as the ingredients besides *Ligusticum, Salvia* Root, Tangkuei and Chrysanthemum. This depends on the different types of eye ailments or diseases. The auxiliary ingredients are Polyacrylic adhesives and Azoo.

Exemplary Manufacturing Process of OCULAX™

Figure 5:
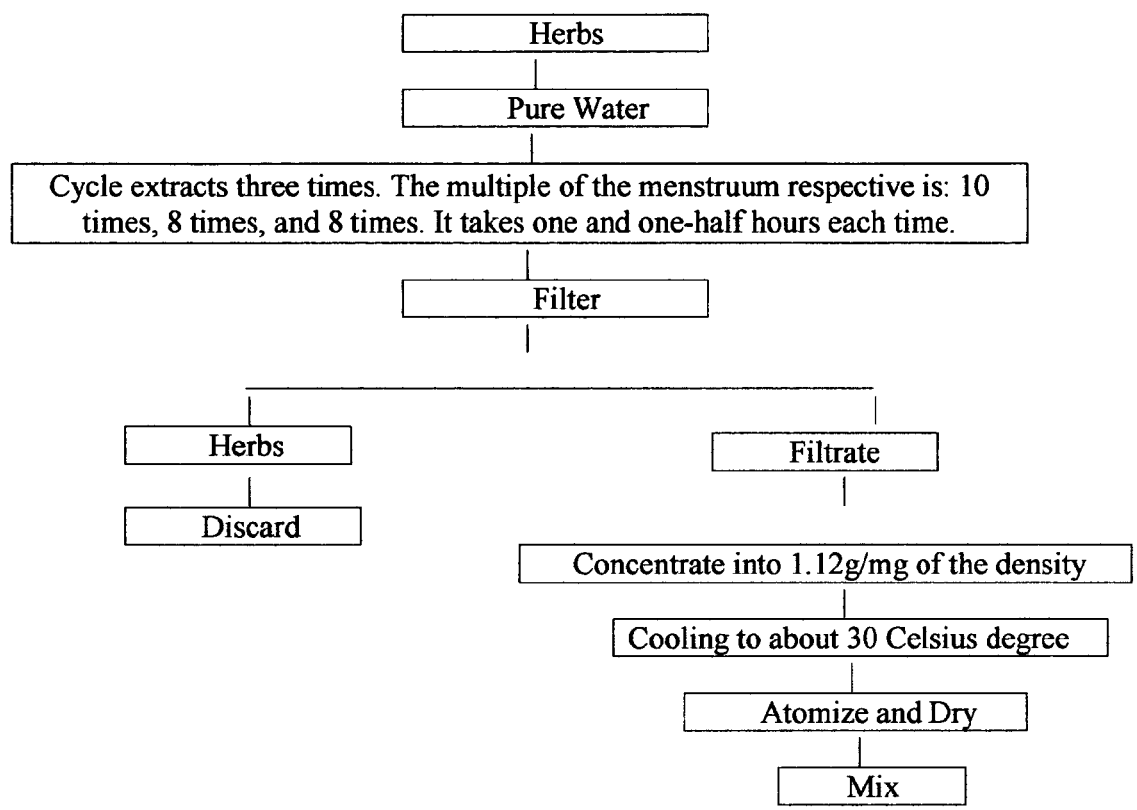
FIG. 5 illustrates an exemplary flow chart for the herbal extraction process in accordance with the present invention.

1. Process of herb extraction: Extract the valid composition from *Ligusticum, Salvia* Root, Tangkuei and Chrysanthemum. Concentrate and dry the extracts and make them into small powder for later use. The flowchart of the herb extraction process is shown in FIG. 5.

2. Process of Polyester thin plastics: First iron the definite-thickness polyester thin plastics by electricity. Second, evenly apply the organic-silicon paste-proofing agent on the polyester thin plastics. Stove the polyester thin plastics for later use.

3. Process of the silk: First, process a special waterproofing on weaved silk. Then plate Aluminum on the silk for later use.

4. Process of the herbs mixture: Weigh certain amount of polyacrylate emulsion. While agitating the polyacrylate, add quantify extracts of *Ligusticum, Salvia* Root, Tangkuei and Chrysanthemum one by one. 60 minutes later, add some trans-derma promoter, wetness retainer and fragrance. Then agitate for 30 minutes. Test the PH value of the solution till the PH value showing at the middle value. At last, filter the solution for later use.

The Manufacturing Process of OCULAX:

A. Herbs Control:

Evenly apply the processed solution on the processed silk by scraping or transfer. Control the quantity of the colloidal substance on the processed silk to no lower than 120 g/square meter. Cover the processed polyester thin plastics and cut it into round standard of 17 mm diameter. After Quality Control inspection, pack it into finished products. The structure is as the follows:

1. Silk Lining
2. Herbs Storage Layer
3. Protection Layer

According to this manufacturing process, the release of herbal extracts is controlled by the transdermal promoter and measurements of nano-processed particles. It also controls the density of the blood medicine so that it can control the pace of the treatment.

B. Controlled Releasing:

First dissolve the herb extracts. Add by evenly applying the processed solution on the processed silk by scraping or transfer. Paste the release control film on the herbs storage layer and evenly apply the sensitivity reduction layer on the release control film layer. Cut it into appropriate standard pieces and cover the processed protection layer. Pack it into completed products. The structure is as the follows:

1. Silk Lining
2. Herb Storage Layer
3. Release Control Layer
4. Sensitivity Reduction Layer
5. Protection Layer Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A patch for applying a medication to an acupoint of a patient's body, the patch having an inner surface for application to the skin of a patient and an outer surface, comprising:
    a lining layer, to protect said medication, the lining layer having an inner surface and an outer surface;
    a storage layer comprising the medication, wherein the storage layer is disposed in communication with the inner surface of the lining layer, and wherein the medication comprises a mixture of extracts of each of four selected herbs, wherein the selected herbs are *Ligusticum, Salvia* root, Tangkuei, and chrysanthemum, and wherein each extract is prepared according to the following process:
        (i) providing the selected herb;
        (ii) adding pure water to the selected herb;
        (iii) extracting components of the selected herb in three cycles, wherein each cycle is performed for one and one-half hours;
        (iv) filtering the water and the selected herb, thereby obtaining a filtrate and an herbal remainder;
        (v) concentrating the filtrate;
        (vi) cooling the concentrated filtrate to about 30° Celsius;
        (vii) atomizing the concentrated filtrate; and
        (viii) drying the concentrated filtrate, thereby obtaining the extract of the selected herb; and
    a self stick material on the inner surface of the patch.

2. The patch of claim 1, further comprising a non-sticking protection layer, releasably affixed to the inner surface of the patch.

3. The patch of claim 1, wherein the self-stick material comprises a polyacrylic adhesive.

4. The patch of claim 1, wherein the storage layer further comprises a nitrogen ketone.

5. The patch of claim 1, wherein the lining layer is a silk lining plated with aluminum.

6. The patch of claim 1, wherein the medication comprises: between 5 mg and 50 mg of the extract of *Ligusticum*; between 5 mg and 50 mg of the extract of *Salvia* root; between 5 mg and 50 mg of the extract of Tangkuei, and between 5 mg and 50 mg of the extract of chrysanthemum.

7. The patch of claim 1, wherein the storage layer comprises an inner surface and an outer surface, further comprising a controlled release layer in communication with the inner surface of the storage layer for controllably releasing the medication into the patient's body.

8. The patch of claim 1, wherein the self-stick material comprises a pressure-sensitive latex.

9. The patch of claim 6, wherein said mixture comprises: 19 mg of the extract of *Ligusticum,* 17 mg of the extract of *Salvia* root, 11 mg of the extract of Tangkuei, and 33 mg of the extract of chrysanthemum.

* * * * *